United States Patent [19]

Beukers et al.

[11] Patent Number: 4,480,334
[45] Date of Patent: Oct. 30, 1984

[54] RADIOSONDE HOUSING

[75] Inventors: John M. Beukers; Christian B. Williams, both of Stony Brook, N.Y.

[73] Assignee: Beukers Laboratories, Inc., St. James, N.Y.

[21] Appl. No.: 389,051

[22] Filed: Jun. 16, 1982

[51] Int. Cl.³ .............................................. H04B 1/034
[52] U.S. Cl. .................................. 455/98; 340/870.1; 455/128
[58] Field of Search ....................... 455/95, 98, 128; 73/170 R; 340/870.1, 601, 602

[56] References Cited

U.S. PATENT DOCUMENTS

| | | | |
|---|---|---|---|
| 2,604,582 | 7/1952 | Hauck et al. | 455/98 |
| 2,939,127 | 5/1960 | Graw | 455/128 |
| 3,028,486 | 4/1962 | Rossi | 455/128 |
| 3,353,100 | 11/1967 | Collins et al. | 455/128 |

*Primary Examiner*—Marc E. Bookbinder
*Attorney, Agent, or Firm*—Hopgood, Calimafde, Kalil, Blaustein & Judlowe

[57] ABSTRACT

A housing for electrical components and equipment sent aloft with a weather balloon to measure atmospheric parameters comprises a light-weight polystyrene case that serves as a shipping container and flight package. The housing also includes an air duct and a humidity sensor in the duct. Means in the duct minimize the reflection of sunlight onto the sensor to maintain at ambient temperature the air which flows over a humidity sensor.

14 Claims, 6 Drawing Figures

RADIOSONDE HOUSING

BACKGROUND OF THE INVENTION

The invention relates to a radiosonde housing.

One known method of measuring atmospheric parameters such as temperature, humidity, and pressure at various altitudes has been the use of a miniature radio transmitter and sensing instruments carried aloft by, for example, an unmanned balloon for transmitting data signals back to earth stations. This transmitter, with accompanying sensing instruments, is generically known as a radiosonde. Current designs employ analog circuitry contained in a relatively large and heavy container. Furthermore, the battery and humidity element necessary for the operation of the radiosonde have been shipped in cans external to the radiosonde, a factor which increases both the shipping weight and volume.

The ambient humidity in a radiosonde is sensed by a humidity sensor which is exposed to the ambient air. However, if the humidity sensor is heated by being exposed to the sunlight, it may well produce erroneous indications of humidity. Ducts employed in the sensor radiosondes were mechanically complex and costly, and introduced an undesirable error in humidity readings by warming the air within the ducts. In addition, these prior art ducts consisted of several individually molded plastic pieces which required assembly.

It is an object of the invention to reduce the shipping weight and volume of a radiosonde.

It is another object of the invention to provide a sturdy, shock absorbent, light weight and inexpensive housing for the flight package which contains the radiosonde.

A still further object of the invention is to provide a radiosone housing which functions as a direct sunlight screen in which the housing integrally forms a duct which allows an adequate air flow across a humidity element while also maintaining the air at, approximately, ambient temperature.

SUMMARY OF THE INVENTION

The present invention provides a light-weight housing formed, for example, from expanded polystyrene beads. This housing serves as a light-weight shipping package which may contain the battery, humidity element, antennas and other eletronic sensing and transmitting equipment. This shipping package also serves as the flight housing for the radiosonde and again has the advantage of being light in weight, sturdy, shock absorbent, and inexpensive. Such factors are particularly important in systems such as radiosondes which must be carried aloft by a balloon and which must also be able to withstand severe wind turbulance. Moreover, since a free fall back to earth after balloon burst destroys a radiosonde after only one use, it is highly desirable to keep the housing cost to a minimum by using inexpensive polystyrene or similar material.

To accurately record humidity, the sensing element in the radiosonde of the invention is shielded from the sun to prevent warming of the element. Thus it is necessary for the humidity sensing element to be placed within a duct so as to be shielded from the sun. The duct is integrally formed within the radiosonde housing, reduces heating of air to a minimum previously unachieved and improves humidity sensor transient response time.

BRIEF DESCRIPTION OF THE DRAWINGS

Other objects and various further features of novelty and invention will be pointed out or will occur to those skilled in the art from a reading of the following specification in conjunction with the accompanying drawings. In these drawings, which show, for illustrative purposes only, preferred forms of the invention.

DESCRIPTION OF THE PREFERRED EMBODIMENTS

Figure 1:
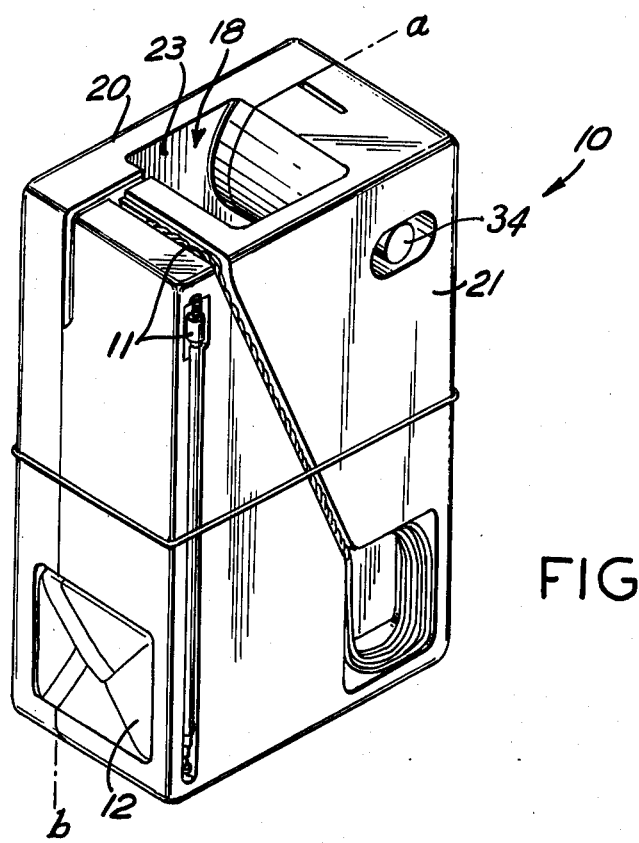
FIG. 1 is a perspective view of a radiosonde prepared for shipping according to the invention.

In the embodiment of the invention depicted in FIG. 1, a radiosonde housing, generally indicated as 10, is shown in its shipping configuration. The navigational and telementry antennas 11, battery 12 and sensors including a humidity sensing element 13 placed in a shipping container 34 are all packed within the housing for shipment. To seal out moisture, the humidity sensing element 13 and its shipping container 34 may also be sealed in a foil packet.

Figure 2:
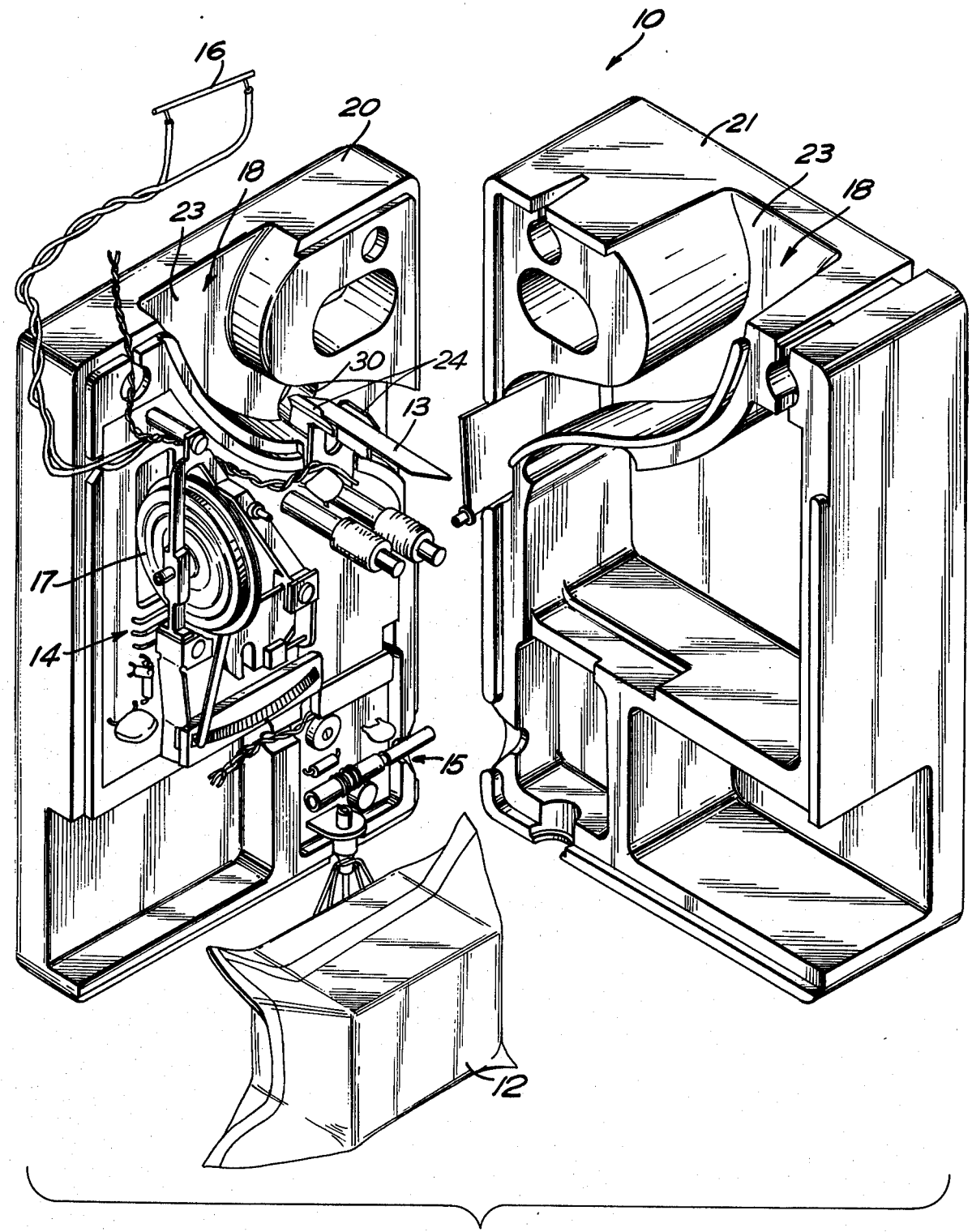
FIG. 2 is a perspective view of the radiosonde housing split along lines a-b of FIG. 1 and showing the internal configuration of the housing.

In FIG. 2, the radiosonde housing 10 is shown divided along lines a-b into a top 21 and bottom 20 so as to show an outer two-piece shell revealing a hollow interior, which contains the components such as the main printed circuit board 14, transmitter 15, battery 12, thermistor sensor 16, humidity sensing element 13, and a pressure sensor 17. The housing 10 also has formed therein an air duct 18, which is described in greater detail in a later part of the specification.

Figure 3:
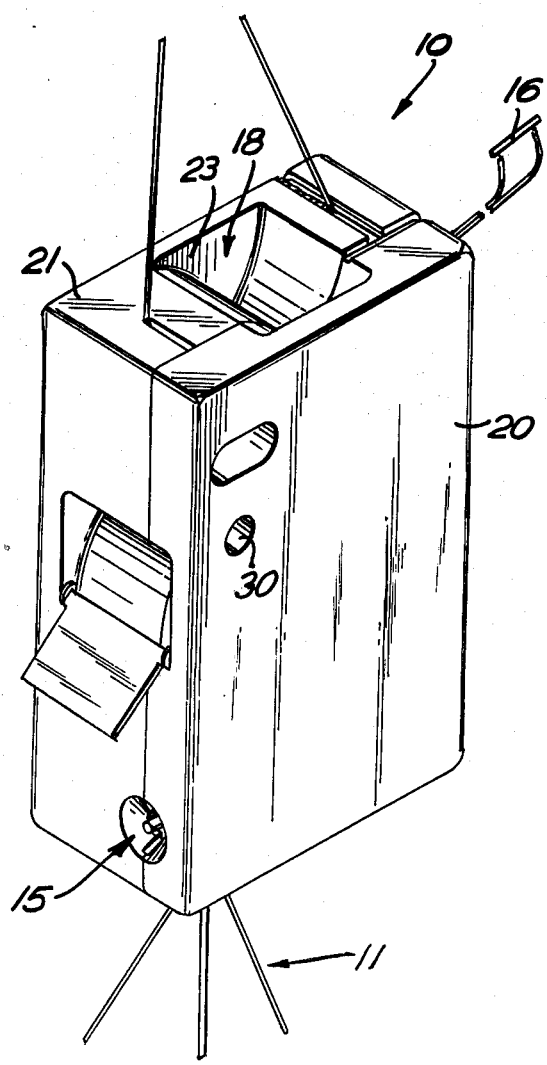
FIG. 3 shows one preferred embodiment of the radiosonde housing of the invention prepared for flight.

In use, the radiosonde housing 10 is shipped to a user in the form depicted in FIG. 1. The user then removes packing restraints such as tapes and bands to release antennas 11, the battery 12 and the humidity sensor container 34. The humidity sensor 13, upon removal from the protective shipping container 34, is positioned in duct 18 through aperture 30 and supported by clips 24 and connected electrically by clips 24 to the main printed circuit board 14. Battery 12 is connected electrically to circuits 14 and 15. The battery may either be an alkaline type, ready for immediate use, or a water-activated unit employing a magnesium cuprous chloride chemical system. The antennas 11, and thermistor 16, are pulled outside of the housing. Finally, the housing 10 is attached to a weather balloon and is carried aloft. The flight configuration of the radiosonde is shown in FIG. 3. It will thus be appreciated that the housing is used both as the shipping package for the radiosonde and also as the housing for the radiosonde when the latter is sent aloft.

The housing 10 can be fabricated from any light-weight, sturdy and inexpensive material having good insulating properties, and may be advantageously made of expanded polystyrene beads. The housing 10 is compact, easy to use and is durable enough for flight.

Figure 5:
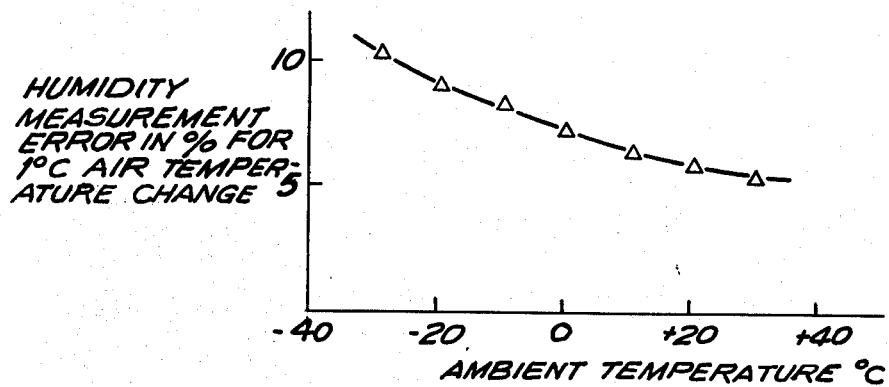
FIG. 5 is a graph comparing humidity measurement error with ambient temperature for a 1° C. air temperature change.

One problem with measuring humidity in prior art radiosondes is the error caused when the air whose humidity is to be measured is warmed by both the sun and the radiosonde itself. This problem can be illustrated by considering the relationship between relative humidity ["RH"] and the saturated water vapor pressure. Relative humidity is determined by the equation $RH = W/WS$ where W equals the weight of water in a given volume and WS equals the weight of water when the same volume is saturated. If the ambient temperature of the air entering the duct is changed by a small amount, the weight of water for saturation is changed resulting in an error in the relative humidity measurement. FIG. 5 shows the humidity measurement error in percent for 1° C. air temperature change verses ambient temperature.

Figure 6:
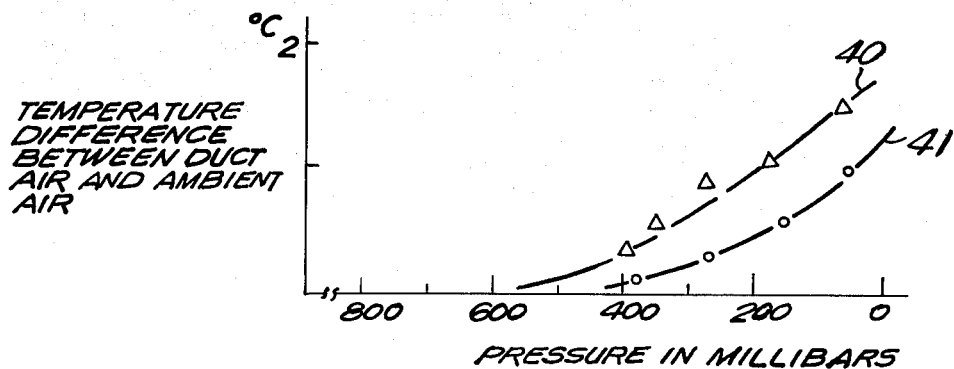
FIG. 6 is a plot of temperature difference between the duct air within the radiosonde of the present invention and a prior art duct arrangement.

One known method of lessening the warming of air has been the use of a duct in which the humidity sensor is positioned. However, the ducts in prior radiosondes still warm the ambient air to a point resulting in appreciable error in humidity measurement. The air duct 18 of the radiosonde of the present invention reduces the humidity measurement error to almost one-half of that obtained in the prior art arrangements. As shown in FIG. 6, wherein plot 40 represents the results obtained with a prior art NWS duct and plot 41 represents the plot obtained with the present invention, the temperature error due to loading above 600 millibars is about one half for the present invention than that exhibited by the prior art duct.

To this end, in contrast to the prior art duct which consisted of several individually molded plastic pieces which also required assembly, the duct 18, according to one aspect of the invention, is molded into the two halves 20 and 21 of the radiosonde housing 10 and does not require separate molding or assembly, which further reduces material and labor cost.

Figure 4:
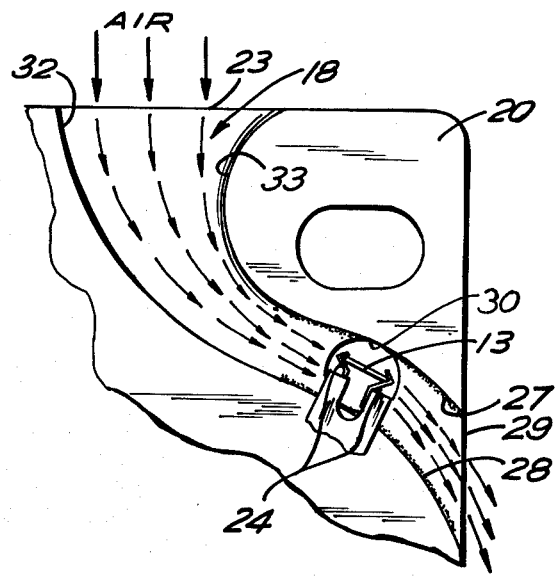
FIG. 4 is an enlarged view of the duct shown in FIG. 2.

The duct 18, as shown in FIG. 4, is molded within the polystyrene housing into a venturi form. The venturi formed duct 18 increases the flow of external air over the humidity sensor 13 mounted within the duct while shielding the sensor 13 from direct solar radiation. Internal surfaces 27 and 28 of the interior wall of duct 18 are blackened to prevent solar radiation reflection onto humidity sensor 13, whereas nonblackened surfaces 32 and 33 remain a light color, such as white, to reflect solar radiation and minimize warming of the interior wall of duct 18 and thus minimize warming of the ambient air adjacent the interior wall. As the housing rises aloft, air is forced into the inlet port 23 of duct 18 and is guided so as to flow across humidity sensor 13, which is longitudinally positioned in the center of the narrowest point of air passage in duct 18 and is maintained in this position by a pair of laterally offset clips 24. The offset clips 24 allow easy external insertion of the humidity sensor 13 through aperture 30 and enable the humidity element 13 to be held orthogonally to the printed circuit board 14. Air leaves duct 18 through outlet port 29. The venturi configuration of duct 18 tapers toward outlet port 29, and sensor 13 is preferably positioned nearer to outlet port 29.

Another improvement resulting from the design of duct 18 is air flow and transient response of the humidity sensor 13. In one set of wind tunnel tests performed on the radiosonde of the invention at an ascent rate of one meter per second, the humidity sensor 13 was placed in a duct designed according to the present invention, and in another set of tests the same humidity sensor 13 was placed in a prior art design employed by the U.S. National Weather Service ["NWS"]. The results of these tests indicate that the transient response time for the duct according to the present invention is equal or faster than that obtained with the prior art duct. A summary of the tests results is as follows:

| Conditions: | 20° C. |  |
| --- | --- | --- |
|  | 1 meter/sec aspiration |  |
|  | 30% RH to saturation |  |
|  | Average of 10 repeated cycles |  |
| Transient Response: |  |  |
|  | DUCT |  |
|  | Present Invention | NWS |
|  | Time in Seconds |  |
| 67% of Final Reading | 0.5 | 0.7 |
| 95% of Final Reading | 1.2 | 1.8 |

The shape of the housing, other than the duct configuration hereinabove described, is illustrative only and it is to be understood that the use of a polystyrene material for construction of the housing is only one preferred embodiment. It will be further understood that whereas the invention has been herein disclosed with respect to one embodiment thereof, these and other variations may be made without departing from the spirit and scope of the invention.

What is claimed is:

1. A radiosonde housing adapted for employment as both a shipping container and a flight package, said housing comprising an outer shell made of a lightweight material and a hollow interior in which sensing and transmitting components are retained for shipment of the radiosonde housing and thereafter for use when said radiosonde housing is in flight;

said radiosonde housing comprising an air flow duct having an inlet port and an outlet port formed in said shell, and a humidity sensing element positioned in said duct intermediate said inlet and outlet ports;

said air flow duct having a venturi configuration in cross-section, tapering toward said outlet port, said humidity sensing element being positioned nearer to said outlet port;

said shell being integrally formed from bottom and top combinable parts, said bottom and top parts, when combined, enclose the sensing and transmitting components therein and form said air flow duct.

2. The radiosonde housing of claim 1, in which said housing is comprised of expanded polystyrene beads.

3. The radiosonde housing of claim 1, further comprising means on an interior wall of said air flow duct for minimizing the amount of incident sunlight reflected onto said humidity-sensing element.

4. The radiosonde housing of claim 3 in which said minimizing means comprises a blackened substance affixed on the interior wall of said air flow duct.

5. The radiosonde housing of claim 1, further comprising means on an interior wall of said air flow duct for reflecting solar radiation entering said duct to minimize heating of said interior wall and thus minimize warming of ambient air adjacent said interior wall.

6. The radiosonde housing of claim 1, further comprising clip means having first and second laterally displaced elements for mounting said humidity-sensing element in said air duct.

7. A radiosonde housing comprising top and bottom parts which enclose sensing and radio transmitting components therein when combined, said combined top and bottom parts integrally forming within said housing a venturi-shaped air flow duct, and a humidity sensor suspended within said venturi-shaped air flow duct, said radiosonde housing being used as both a shipping container and a flight package.

8. The radiosonde housing of claim 7, further comprising means on an interior wall of said air flow duct for preventing sunlight from being reflected onto said humidity-sensor.

9. The radiosonde housing of claim 8, in which said means for preventing sunlight reflection comprises a blackened substance affixed on said interior wall of said air flow duct.

10. The radiosonde of claim 7, further comprising means on an interior wall of said air flow duct for reflecting solar radiation entering said duct to minimize heating of said interior wall and thus minimize warming of ambient air adjacent said interior wall.

11. The radiosonde housing of claim 7, in which said housing is comprised of expanded polystyrene beads.

12. A radiosonde housing adapted for employment as both a shipping container and a flight package, said housing comprising an outer shell made of a lightweight material and a hollow interior in which sensing and transmitting components are retained for shipment of the radiosonde housing and thereafter for use when said radiosonde is in flight;

said radiosonde housing comprising an air flow duct having an inlet port and an outlet port formed in said shell, and a humidity sensing element positioned in said duct intermediate said inlet and outlet ports;

said radiosonde housing further comprising means on an interior wall of said air flow duct for minimizing the amount of incident sunlight reflected onto said humidity-sensing element.

13. The radiosonde housing of claim 12 in which said minimizing means comprises a blackened substance affixed on the interior wall of said air flow duct.

14. A radiosonde housing adapted for employment as both a shipping container and a flight package, said housing comprising and outer shell made of a lightweight material and a hollow interior in which sensing and transmitting components are retained for shipment of the radiosonde housing and thereafter for use when said radiosonde housing is in flight;

said radiosonde housing comprising an air flow duct having an inlet port and an outlet port formed in said shell, and a humidity sensing element positioned in said duct intermediate said inlet and outlet ports;

said humidity-sensing element being mounted in said air duct by clip means having first and second laterally displaced elements;

said radiosonde housing having an additional aperture through which said humidity sensor is externally inserted into said clip means.

* * * * *

UNITED STATES PATENT AND TRADEMARK OFFICE
CERTIFICATE OF CORRECTION

PATENT NO. : 4,480,334
DATED : October 30, 1984
INVENTOR(S) : John M. Beukers and Christian B. Williams It is certified that error appears in the above-identified patent and that said Letters Patent are hereby corrected as shown below:

In column 6, line 17, (line 3 of claim 14), "and" should be -- an --.

Signed and Sealed this

Thirtieth Day of April 1985

[SEAL]

Attest:

DONALD J. QUIGG

*Attesting Officer*   *Acting Commissioner of Patents and Trademarks*